United States Patent [19]

Kegelman et al.

[11] Patent Number: 4,958,932
[45] Date of Patent: Sep. 25, 1990

[54] OPTICAL MEASURING APPARATUS

[75] Inventors: Jerry T. Kegelman; Joseph C. Kroutil; Rodney Lusk, all of St. Louis County, Mo.

[73] Assignee: McDonnell Douglas Corporation, St. Louis, Mo.

[21] Appl. No.: 234,169

[22] Filed: Aug. 18, 1988

[51] Int. Cl.⁵ ............................................. G01B 11/00
[52] U.S. Cl. .................................... 356/383; 356/372; 128/6; 350/96.25
[58] Field of Search ............... 356/372, 378, 379, 383, 356/384, 439, 227, 73.1; 350/96.24, 96.25, 96.26; 128/4–6

[56] References Cited

U.S. PATENT DOCUMENTS

4,660,982  4/1987  Okada .................................. 356/383

Primary Examiner—Richard A. Rosenberger
Assistant Examiner—Hoa Pham
Attorney, Agent, or Firm—Gravely, Lieder & Woodruff

[57] ABSTRACT

An apparatus for measuring the distance between two locations on a surface within a cavity includes a sheath which is inserted into the cavity and a scope which extends through the sheath. Through the scope, one from a remote location may observe the surface as well as reference marks which appear within the field of view on each side of the optical axis. These reference marks are aligned with opposite sides of that which is to be measured on the surface. In addition, the apparatus includes two point sources of light located along opposite sides of the scope with each source being located behind a lens that is presented toward the surface which is observed within the field of view. The lenses project their sources of light into the field of view as rays which come into focus on the surface. Under these conditions it is possible to ascertain the distance between the two regions of the surface at which the reference marks appear; that is the distance between the opposite sides of that which is under observation.

22 Claims, 7 Drawing Sheets

OPTICAL MEASURING APPARATUS

BACKGROUND OF THE INVENTION

This invention relates in general to measuring, and more particularly to an apparatus for measuring the space between locations on surfaces without actually contacting those surfaces.

In certain medical procedures it is desirable to know the width of a body canal or passage or to know the size of an obstruction within the same. For example, when placing an endotracheal tube, the physician should have a reasonable idea as to the size of the trachea so as to be able to select a tube of appropriate diameter. Similarly, premature infants sometimes experience difficulty breathing, and in such situations it is helpful to know the size of the infant's trachea.

An instrument known as a bronchoscope exists for observing the surface that lines the trachea, and this device not only possesses the optics for making the observation, but also transmits light to and projects it onto the surface to provide enough illumination for a meaningful observation. Even so, a bronchoscope does not have the capacity to measure the width or diameter of the passage which is observed through it.

Other devices or scopes exist for illuminating and observing the walls of other body canals, and these scopes likewise do not provide any means for measuring the width of the canal so observed or lesions on the linings of body cavities. Irrespective of the type of scope, it is usually not inserted directly into the canal, but instead through a sheath which is first placed in the canal.

The present invention provides a bronchoscope or similar scope with the capacity to measure the width of a body canal or obstruction in it in addition to observing the canal, and the measurement is made without actually contacting the surfaces from which the measurements are taken. Not only is the device suitable for use by the medical profession, but with slight adaptations, it finds utility in other fields as well, indeed in practically any circumstance where a measurement must be taken from the interior of a tube or cavity. In essence, the apparatus is an optical caliper.

DESCRIPTION OF THE DRAWINGS

In the accompanying drawings which form part of the specification and wherein like numerals and letters refer to like parts wherever they occur

DETAILED DESCRIPTION

Referring now to the drawings, an apparatus A (FIG. 1) enables one to observe and measure the interior of a passage or cavity B from deep within the cavity B, or to observe and measure an object or lesion D along the surface of the cavity B. To this end the apparatus A contains optics which illuminate the cavity B in the region to be observed, and of course optics which enable one to observe the illuminated region from beyond the end of the passage. In addition, the apparatus A possesses optics which, by means of projected light, enables one to measure the width of the cavity B or lesion D at the illuminated region, all without actually contacting the surface of the cavity B or lesion D, at least in the region to be measured. The cavity B may be a body canal such as the trachea, intestine or colon, or it could be the interior of a body organ such as a stomach or uterus. The apparatus A possesses three basic components, namely a sheath 2 which is small enough to fit into and move through the cavity B, an elongated scope 4 which extends through the sheath 2, and an optical measuring system 6 for measuring the width of the cavity B or lesion D beyond the end of the scope 4 and sheath 2.

Figure 2:
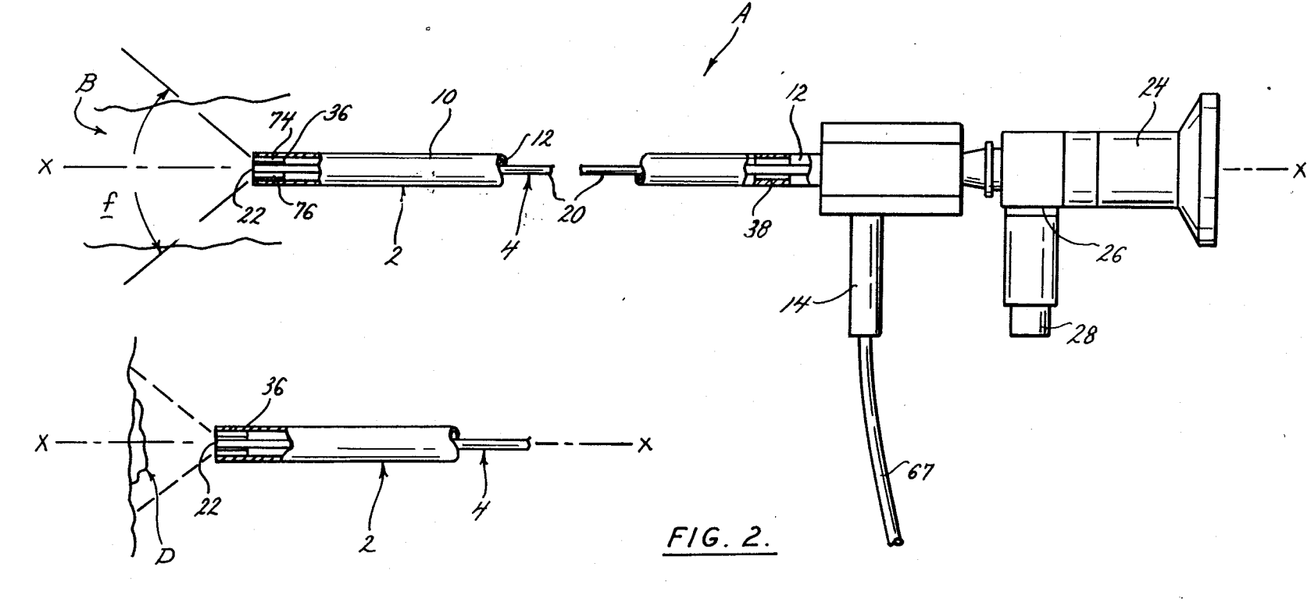
FIG. 2 is a side elevational view of the optical measuring apparatus.

Considering the sheath 2 first, it essentially constitutes nothing more than a thin wall tube 10 having smooth interior and exterior surfaces (FIG. 2). The outside diameter of the tube 10 is less than that of the cavity B or is at least less than the diameter to which the cavity B can be expanded, and its length is great enough to reach from the exterior of the body all the way to the region of the cavity B which is to be observed. Thus, the tube 10 has a distal end which locates in the cavity B when the apparatus A is in use and a proximal end which remains outside of the cavity B. The inner diameter of the tube 10, on the other hand, is substantially larger than the outer diameter of the scope 4, so that an annular channel 12 exists between the sheath 2 and the scope 4. Where the apparatus A is used for examination of the trachea, the annular channel 12 serves to conduct air into and out of the lungs in the portion of the trachea that is occupied by the apparatus A. In addition, the sheath 2 has an optical port 14 located on the tube 10 near the proximal end thereof.

Figures 1, 8, 9:
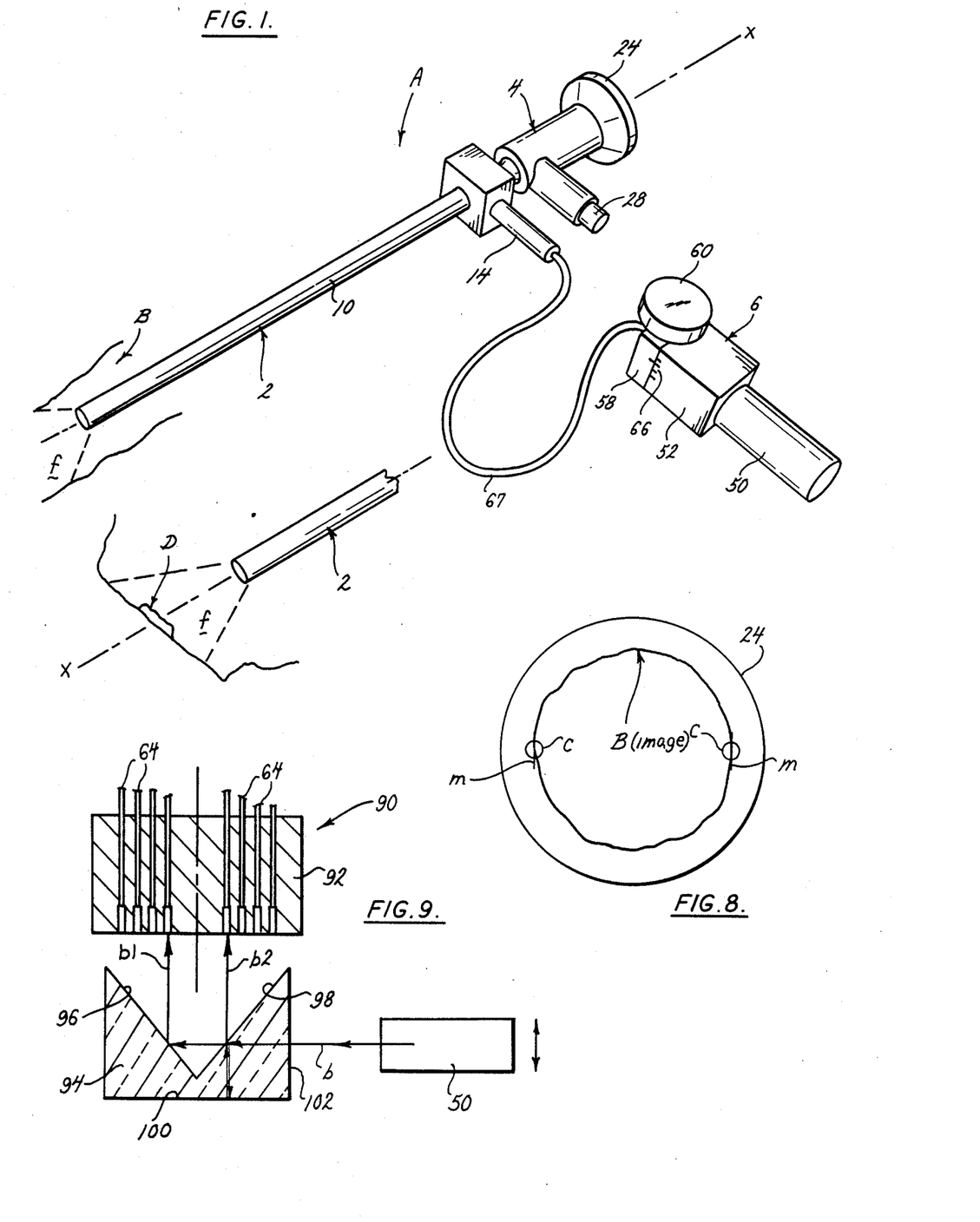
FIG. 1 is a perspective view of an optical measuring apparatus constructed in accordance with and embodying the present invention.
FIG. 8 illustrates a view one might observe through the eyepiece of the optical measuring apparatus.
FIG. 9 is a schematic sectional view showing a modified optical measuring system for the apparatus.

The elongated scope 4 (FIG. 2) is typical of various scopes used for examining body passages and canals. Where the apparatus A is employed for examination of the trachea, the scope may be nothing more than a simple bronchoscope. As such, the scope 4 includes a tube 20 of relatively small diameter—a diameter considerably smaller than the inside diameter of the encircling tube 10 for the sheath 2. At its distal end, that is the end which enters the body cavity B, the tube 20 carries an objective lens 22. At its proximal end it is fitted with an eyepiece 24 which aligns with the objective lens 22 along an optical axis x. The two are optically connected by either optical fibers or quartz rods (neither shown). The objective lens 22 produces an image of the region of the cavity B toward which it is presented, and the eyepiece 24 enables one to observe that image from beyond the confines of the cavity B (FIG. 8). The lens 22 has a divergent field of view f, one in which the object appears to be located considerably farther from the lens 22 than it actually is. As such it could be characterized as a wide angle lens. In addition, the tube 20 immediately beyond the eyepiece 24 is fitted with an optical port 26 to which a source 28 of light is attached. The light illuminates a bundle of optical fibers (not shown) which pass through the port 26 into the tube 20 and thence along the inside of the tube 20 to its distal end. The fibers of the bundle terminate alongside the objective lens 22, so that light from the source 28 is projected into the field of view f where it illuminates the surface that lines the cavity B.

The scope 4 differs from a conventional bronchoscope or similar scope in that it has inscribed within its eyepiece 24 two target marks m (FIG. 8) which lie on each side of optical axis x and of course appear to be within the field of view f. Indeed, the marks m appear near the periphery of the field of view f, but are nevertheless always visible through the eyepiece 24, so that light reflected from the lining of the cavity B or from a lesion D along rays n (FIG. 7) will appear in the eyepiece at marks m. The angle between the two marks m is less than that of the field of view f, and that angle of course remains constant irrespective of the distance between the objective lens 22 and the object or surface under observation. Moreover, the angle between the two marks m is bisected by the optical axis x.

The scope 4 remains in fixed position within the tube 10 of the sheath 2, and cannot be moved either radially or axially, for it is held within bushings 36 and 38 (FIG. 2) which fit into opposite ends of the tube 10, the former being near the distal end and the latter near the proximal end. Each bushing 36 and 38 contains axial channels 40 of its own, and these channels extend from one end of each bushing 36 and 38 to the other, so the bushings 36 and 38 do not block the annular channel 12 which exists between the tube 20 of the scope 4 and the tube 10 of the sheath 2. As a result, air will pass through the tube 10—and so can auxiliary equipment such as suction tubes, sutures and surgical scissors.

Figure 4:
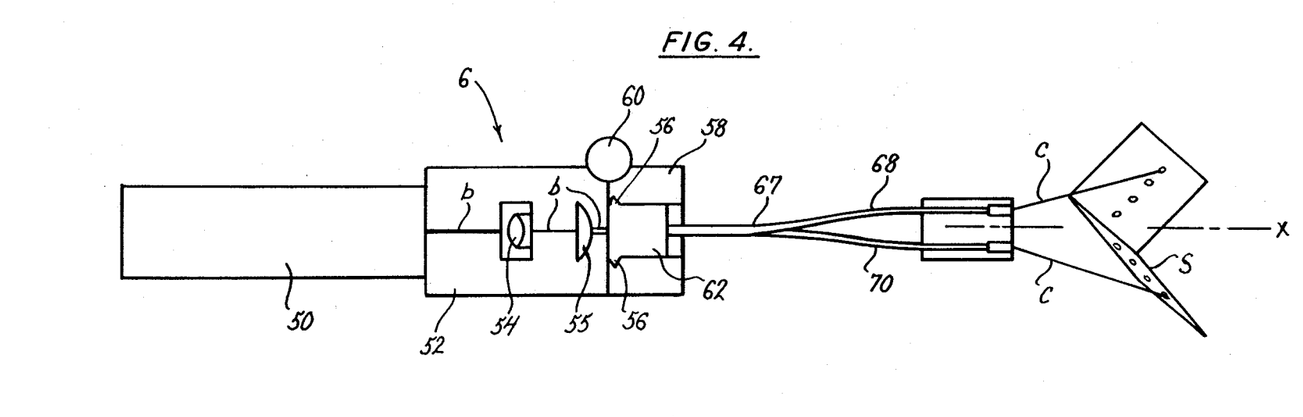
FIG. 4 is a schematic view showing the laser light source, the lenses, and the header block of the optical system.

The optical measuring system 6 projects light forwardly into the field of view f for the objective lens 22 of the scope 4, and by relating the light so projected to the marks m which are visible through the eyepiece 24 of the scope 4, one looking through the scope 4 can ascertain the width of the body cavity B or a lesion D on its lining. At one end of the optical system 6 is a light source such as low power laser tube 50 (FIGS. 1 & 4) which is capable of generating a beam b of light which can be precisely focused. The laser tube 50 is attached to a housing 52 that may be located remote from the sheath 2, or may be attached directly to it, and the housing 52 in turn carries a condensing lens 54 and a plano-cylindrical lens 55 through which laser tube 50 projects the beam b of laser light in that order (FIG. 4). Immediately beyond the lens 55 the housing 52 is provided with a slideway 56 which is oriented perpendicular to the beam b and parallel to the cylindrical axis of the lens 55. The slideway 56 in turn carries a slide 58 which is moved by a thumb screw 60 connected between it and the housing 52. Thus, when the screw 60 is turned, the slide 58 moves relative to the lenses 54 and 55 and to the light beam b. The movement is, of course, perpendicular to the beam b.

Figure 5:
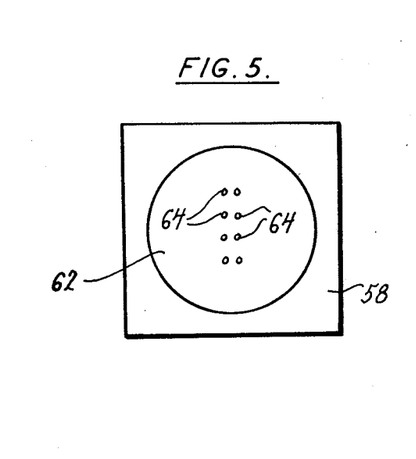
FIG. 5 is a sectional view taken along line 5—5 of FIG. 3.
Figure 6:
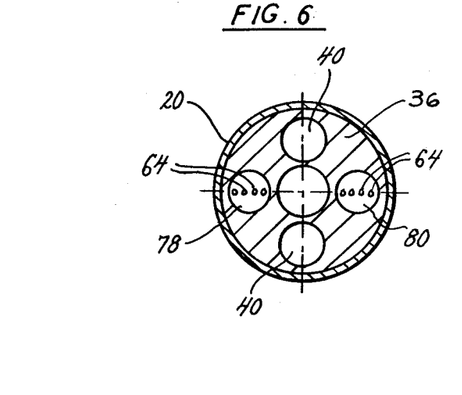
FIG. 6 is a sectional view taken along line 6—6 of FIG. 3.

The slide 58 carries a header block 62 (FIGS. 3–5) which serves as the anchor for the ends of several optical fibers 64, with each fiber 64 being parallel to the beam within the block 62 and further having its end presented toward the lens 55. Moreover, the fibers 64 at the blocks 62 are arranged in pairs, with the fibers 64 of each pair being located side-by-side. The several pairs of fibers 64, on the other hand, are arranged in series, one after the other, along a line that lies parallel to the slideway 56 and the cylindrical axis of the lens 55 as well. The beam b is centered with respect to the line along which the pairs of fibers 64 lie, and the plano-cylindrical lens 55 spreads it enough transversely so that it illuminates the fibers 64 of any pair with which it aligns, but not the fibers 64 of adjacent pairs. The particular pair which is illuminated depends on the position of the slide 58, and that in turn is controlled by the thumb screw 60. By turning the screw 60, different pairs of fibers 64 come into alignment with and are illuminated jointly by the beam b, but only one pair of fibers 64 is illuminated at a time. The slide 58 possesses a scale 66 (FIG. 1) which in effect designates the pair of fibers 64 that is illuminated by the beam b, but the scale 66 is marked otherwise—indeed in units of linear measure.

Figure 3:
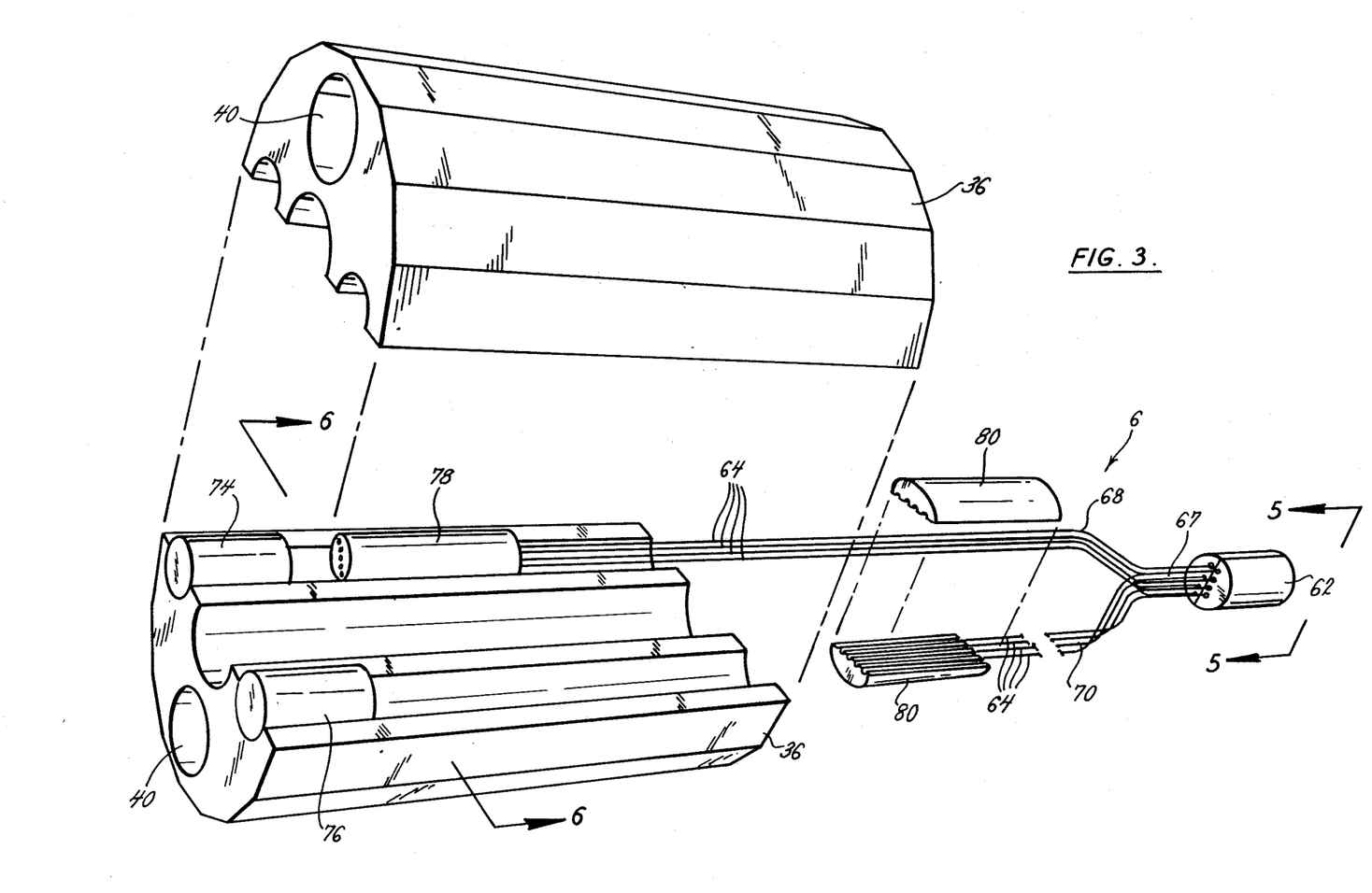
FIG. 3 is a perspective view of the head and terminal blocks together with the optical fibers for the optical measuring system of the apparatus.

The fibers 64 emerge from the housing 50 in a flexible bundle 67 (FIG. 2) that passes into the sheath 2 through the optical port 14 on the tube 10 thereof, and within the tube 10 the fibers 64 are arranged in two groups 68 and 70, the former containing the fibers 64 that are along one side of the array in the block 62, that is to one side of the line with which the beam b is centered, and the latter containing the fibers 64 that are along the other side of that array (FIG. 3). In other words, for each pair of fibers 64 within the block 62, one fiber 64 of the pair is within the group 68 and the other is within the group 70.

The other end of the optical measuring system 6 exists within the bushing 36 in the form of lenses 74 and 76 which are presented forwardly toward the field of view f observed through the objective lens 22 of the scope 4. The lenses 74 and 76 are arranged symmetrically about the optical axis x of the scope 4, that is to say they are located 180° apart and are spaced equidistantly from the optical axis x. Behind the lenses 74 and 76 lie optical terminal blocks 78 and 80 respectively, and it is to these blocks 78 and 80 that the fibers 64 of the two groups 68 and 70 of optical fibers 64 extend. In particular, the fibers of the group 68 extend to the block 78 that is behind the lens 74, while the fibers of the group 70 extend to the block 80 that is behind the lens 76. The lenses 74 and 76 may be gradient refractive index lenses, sometimes called GRIN lenses.

Figure 7A:
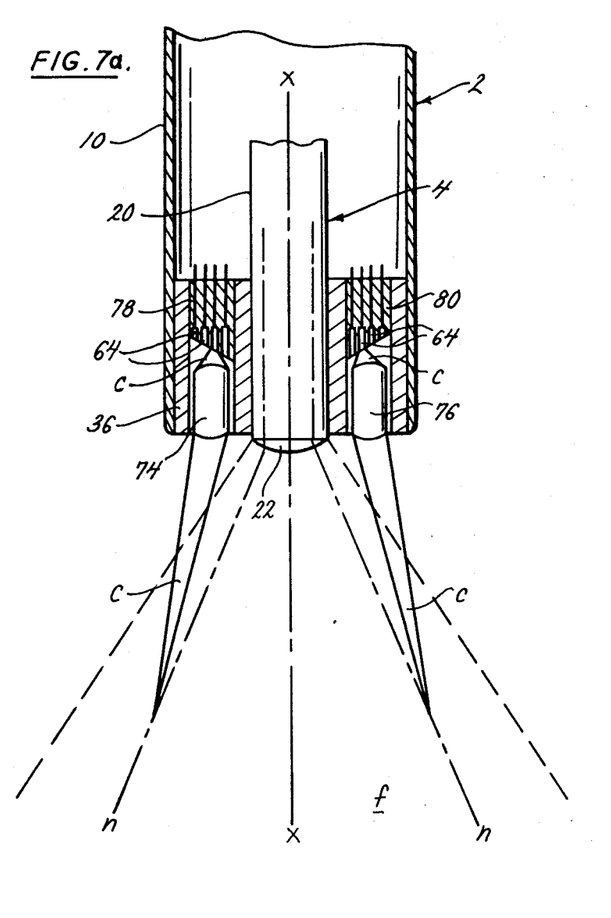
FIGS. 7a and b are ray diagrams showing the light focusing at different locations in the field of view.

Considering the block 78 first, the fibers 64 of the group 68 are at their ends anchored within the block 78 where they lie parallel to each other and likewise parallel to the optical axis x (FIG. 3). Moreover, the end faces of the several fibers 64 are presented toward and exposed to the lens 74, with the fiber 64 that is closest to the optical axis x having its end located closest to the back of the lense 74 and the remaining fibers 64 being located progressively farther from the back of the lens 74. Thus, when the opposite end of any one of the fibers 64 is illuminated by the beam b, that fiber 64 will project a beam c into and through the lens 74 (FIG. 7a). Furthermore, the fiber 64 that is located at one end of the array within the header block 62 of the slide 58 is located closest to the optical axis x in the terminal block 78, while the fiber 64 that is located at the opposite end of the array in the header block 62 is located farthest from the optical axis x in the terminal block 78. The remaining fibers 64 maintain the same order between the endmost fibers 64, that is the order from end-to-end within the terminal block 78 is the same as within the header block 62.

Figure 7B:
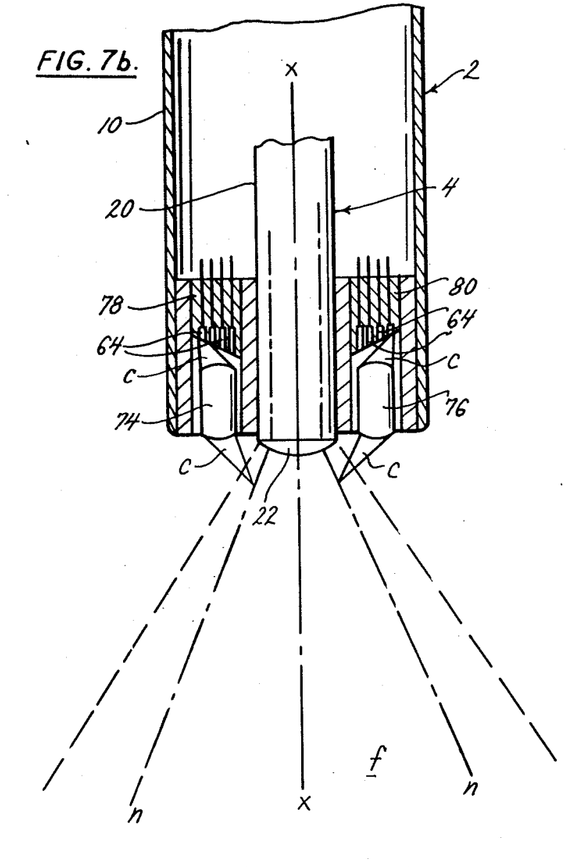

The fibers 64 that pass through the other bundle 70 are arranged in a like manner within the terminal block 80, their ends likewise being located at progressively greater distances from the back of the lens 76 with fiber 70 that is closest to the optical axis x being also closest to the back of the lens 76 (FIG. 7a). Moreover, the fiber 64 that is located closest to the optical axis x within the terminal block 80 is located at the same end of the array in the header block 62 as the fiber 64 that is located closest to the optical axis x in the terminal block 78. Thus, the fibers 64 of any pair within the header block 62 will terminate within their respective terminal blocks 78 and 80 at equal distances from the optical axis x. As a consequence, the laser beam b upon entering the ends of any pair of bundles 64 within the entry block 62 will emerge from the bundles 64 as a pair of beams c spaced equidistantly from the optical axis x. The beams c pass into and through their respective lenses 74 and 76 (FIGS. 7a, b).

Each lens 74 and 76 functions like a double convex lens in that the image produced by it is real and inverted, assuming of course that the object is beyond the focal point of the lens. The object in this instance is the end of the illuminated fiber 64, and the ends of all of the fibers 64 are located slightly beyond the focal points of their respective lenses 74 and 76, notwithstanding the variances in spacing between the ends of the fibers 64 and the two lenses 74 and 76 behind which they terminate. Indeed, the ends of all of the fibers 64 are arranged so that light emitted from them, after passing through the lenses 74 and 76, will come into focus somewhere along the diverging rays n which represent the angle defined by the marks m. Thus, if one of the fibers 64 in the terminal block 78 is illuminated from its other end by the laser tube 50, a beam c will emerge from that fiber 64 in the form of rays which pass through the lens 74 to come into focus beyond the lens 74 where the rays converge to produce a real image (FIGS. 7a, b), and that image will be visible, provided that a surface exists from which the focused or nearly focused rays may reflect (FIG. 8). The outermost fiber 64 in the terminal block 78 produces a focused point of light closest to the optical axis x and also closest to the distal end of the scope 4 (FIG. 7b), whereas the innermost fiber 64 in the block 78 produces a focused point farthest from the optical axis x as well as farthest from the distal end of the scope 4 (FIG. 7a). The same holds true with regard to the beam c that passes through the other lens 76. Thus, two points come into focus or near focus simultaneously within the field of view, one from the beam c passing through the lens 74 and the other from the beam c passing through the lens 76, and these points are spaced equidistantly from the optical axis x and the end of the scope 4 (FIG. 8) and lie along the rays n representing the marks m on the eyepiece 24.

When the thumb screw 60 is turned, the beam b illuminates different pairs of fibers 64, and as a consequence, the locations in which the beams c come into focus change. If one were to place a V-shaped screen s (FIG. 4), such as a piece of paper, across the field of view at the appropriate distance from the lenses 74, 76, the points of light would appear to move across the screen, either toward or away from the optical axis x and likewise toward and away from the distal end of the scope 4 (FIG. 2). This of course derives from the fact that rotation of the thumb screw 60 moves the laser beam b from one pair of fibers 64 to the next and each pair splits apart beyond the header block 62 to terminate behind a different lens 74 and 76. The two beams c when projected onto the screen s are within field f of view for the objective lens 22 of the scope 4 and can be observed through the eyepiece 24 of the scope 4 along with the two reference marks m. The points created on the screen s by the two beams c can be moved inwardly and outwardly until they are superimposed on or located close to the reference marks m. The scale 66 on the slide 58 at the housing 52 is calibrated in units of linear measure, and by reading the distance on the scale 66, it is possible to determine the spacing between the two places on the screen s where the points of focused light are superimposed on reference marks m.

In actual practice, a screen s in the sense that it was previously described does not exist—that is as a V-shaped piece of paper—but a screen resides in the surfaces of the body cavity B. The sheath 2 is inserted into the cavity B, distal end first, until a region of interest comes into view through the eyepiece 24, this region being illuminated for purposes of observation by the light source 28 on the scope 4. Next, the scope 4 is adjusted axially until the reference marks m align with the walls of the cavity B in the region where the width of the cavity B is to be measured or with the boundary of the lesion D that is to be measured. Thereupon, the laser tube 50 is energized so that it projects a beam b through the lenses 54 and 55 and onto the header block 62. The thumb screw 60 is turned until the two lenses 74 and 76 in the bushing 36 cast beams c of light which come into focus as points of light c on the surface or wall that is to be measured (FIG. 8), and indeed the points c are in effect moved inwardly and outwardly until they align with the reference marks m, at least from the standpoint of being observed through the eyepiece 24 of the scope 4. The scale 66 is read and the distance appearing thereon is the spacing between those surfaces or boundary at which the reference marks m appear.

The apparatus A may be provided with a modified optical measuring system 90 for introducing the beam b into the ends of the fiber bundles 64 (FIG. 9). The modified system 90 contains a header block 92 in which the ends of the fibers 64, instead of being arranged in pairs as in the block 62, are arranged in single line as in the bushing 36 at the distal end of the sheath 2. The system 90 further contains a beam splitter 94 which is located between the laser tube 50 and the header block 92. The beam splitter 94 is actually a prism having front faces 96 and 98 which diverge from an apex and are located in front of a reflective back face 100. The two front faces 96 and 98, which are presented toward the entry block 92, are oblique to the back face 100, and the side face 102 as well, whereas the side face 102 is perpendicular to the back face 100. Moreover, the side face 102 is presented toward the laser tube 50 such that the beam b is oriented perpendicular to that face. Indeed, the beam b enters the beam splitter 94 at the side face 102 and progresses through it parallel to the back face 100 until it encounters the front face 98. Here the beam b splits into two beams b1 and b2. The beam b1 passes through the face 98 to the face 96, from which it is reflected to the array of fibers 64 exposed on one side of the entry block 92. The beam b1 illuminates one of those fibers 64. The beam b2, on the other hand, is reflected at the front face 98, it being directed backwardly to the back face 100 at which it is again reflected, this time forwardly parallel to the reflected portion of the beam b1. The beam b2 leaves the splitter 94 and falls upon the end of one of the fibers 64 in the other array of fibers 64. Indeed, the fiber 64 which is illuminated by the beam b2 corresponds in position to the fiber 64 which is illuminated by the beam b1.

The laser tube 50 is not fixed in position with respect to the beam splitter 94, but instead may be shifted parallel to the two beams b1 and b2 after they have emerged from the beam splitter 94. This is has the effect of moving the emerged beams b1 and b2 together or apart, for it changes the location at which the coherent beam b strikes the face 98. Indeed, the laser tube 50 is mounted on a slide which moves relative to the splitter 94, and the position of the slide is controlled by a thumb screw. Of course as the split beams b1 and b2 move apart or together they illuminate different fibers 64, but the arrangement is such that only two fibers 64 are illuminated simultaneously, one in each array of fibers 64, and the fibers 64 which are illuminated correspond in position within their respective arrays. The effect, is thus the same as illuminating two side-by-side fibers 64 with a single beam b as occurs along the header block 62 of the optical system 6.

A modified optical measuring apparatus E (FIGS. 10 & 11) operates somewhat differently than the apparatus A, irrespective of which measuring system 6 or 90 is used, yet performs the same measurements. The apparatus E, like the apparatus A, utilizes the scope 4, but in the apparatus E, the scope 4 extends through a sheath 110 composed of concentric tubes 112 and 114. The inner tube 112 possesses an inside diameter somewhat greater than the outside diameter of the scope 4, so that when the scope 4 is within it a passage large enough to conduct fluids, such as air, exists between the scope 4 and the inner tube 112. The outer tube 114, of course, fits around the inner tube 112, there being an annular space between the two, and near its distal end, the wall thickness of the outer tube 114 is reduced, with the transition being at a beveled shoulder 116.

The concentricity between the distal ends of the tubes 112, 114 is maintained by a bushing 118 which is contained within the region of reduced wall thickness for the outer tube 114, yet is fixed in position with respect to the inner tube 112. The outer tube 114, however, is free to both rotate and shift axially with respect to the bushing 118 and the inner tube 112 as well. The bushing 118 contains two lenses 120 and 122 which are located 180° apart around the common axis of the tubes 112, 114, that is the optical axis x, and are further exposed at the distal ends of the two tubes 112, 114. The bushing 118 projects rearwardly beyond each lens 120, 122 where it is provided with slots 124 (FIG. 11) which are directed radially with respect to the optical axis x.

Figures 10, 11:
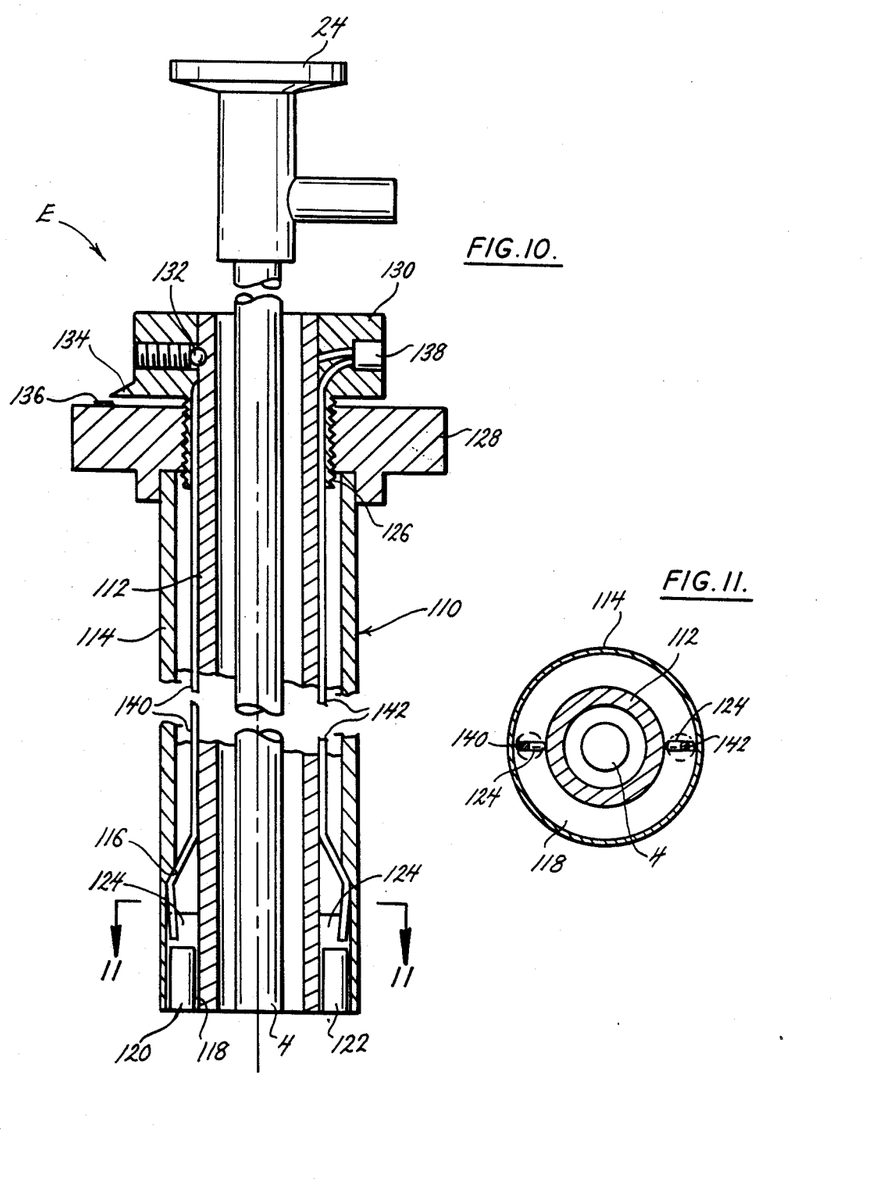
FIG. 10 is a longitudinal sectional view of a modified optical measuring apparatus.
FIG. 11 is a sectional view taken along line 11—11 of FIG. 10.

At their proximal ends the two tubes 112, 114 are united through a threaded sleeve 126, which fits over and is attached to the inner tube 112, and a nut 128 which threads over the sleeve 126 and is attached to the outer tube 114. Thus, when the nut 128 is turned with respect to the inner tube 112, the outer tube 114 shifts axially with respect to the inner tube 112. Actually, the inner tube 112 projects somewhat beyond the nut 128 at the proximal end of the outer tube 114 where it is fitted with a removable head 130 that is normally secured in place on the inner tube with a detent 132. The head 130 possesses a pointer 134 which projects over a scale 136 on the end of the nut 128 so that the scale 136 moves beneath the pointer 134 when the nut 128 is turned. The scale 136 is graduated in units of linear measure.

The head 130 contains an optical port 138 to which a light source in the form of an array of optical fibers 140 is connected, and that light source may be a laser. Leading from the optical port 138 are two optical fibers 140 and 142. Each passes through the threaded sleeve 126 and along the outer surface of the inner tube 112, to which it is bonded by a suitable adhesive or other bonding agent, at least down to the region of the beveled shoulder 116. Indeed, the fibers 140 and 142 are arranged 180° apart along the tube 112 and extend axially toward the two slots 124 in the bushing 118, with the fiber 140 aligning with one slot 124 and the fiber 142 with the other. Slightly before the beveled shoulder 116, the fibers 140 and 142 flare outwardly away from the inner tube 112 and bear against the shoulder 116, being held against the shoulder 116 by their own natural bias or resiliency. From the shoulder 116, the fibers 140 turn axially and project into the radial slot 124 behind the lens 120, whereas the fibers 142 turn axially and project into the slot behind the lens 122.

The arrangement is such that when the outer tube 114 is rotated with respect to the inner tube 112, the axial position of the shoulder 116 relative to the fibers 140 and 142 and the bushing 118 at the end of the inner sleeve 112 changes, and this forces the ends of the fibers 140 and 142 to move radially inwardly or outwardly in their respective slots 124 in the bushing 118. For example, when the nut 128 is turned down over the threaded sleeve 126 so that it moves away from the head 130, the beveled shoulder 116 will move toward the bushing 118 and force the ends of the fibers 140 and 142 radially inwardly in the slots 124, that is toward the optical axis x. On the other hand, when the nut 128 is rotated in the opposite direction, the beveled shoulder 116 moves away from the bushing 118, allowing the ends of the optical fibers 140, 142 to move radially outwardly in the slots 124 under the natural bias of the fibers 140, 142.

The simultaneous movement of the ends of the fibers 140, 142 in the slots 124 of the bushing 118 equates with the illumination of the different optical fibers 64 in the optical measuring system for the apparatus A. Again, the marks m on the scope 4 are aligned with points of light derived from the optical fibers 140, 142, that is from the beams coming into focus beyond lenses 120, 122 through which they pass. The markings on the scale 136 correlate with the spacing between the ends of the two optical fibers 140, 142 which in turn correlates to the spacing between the points of light.

Another modified optical measuring apparatus F (FIGS. 12 & 13) likewise uses a pair of carefully focused light beams to measure transversely with respect to the optical axis x of the device, but the beams cross and indeed focus at a common point along the optical axis x. The apparatus F likewise has a sheath 150 and a scope 152 which extends through the sheath 150 and is centered with respect to it by a bushing 154 located at the distal ends of the two.

Figure 13:
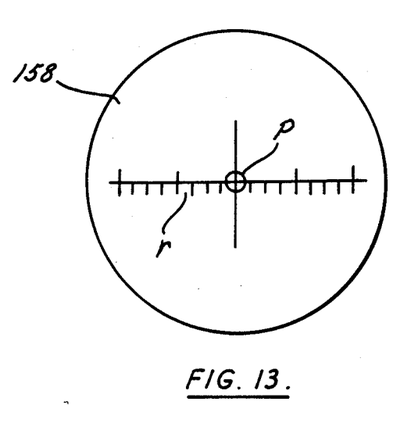
FIG. 13 is a view through the eyepiece of the apparatus shown in FIG. 12.

The scope contains an objective lens 156 and an eyepiece 158, and the latter, instead of having two marks m etched into it, has a full scale r extending totally across it at the optical axis x. The scale r is graduated in units of linear measure.

Figure 12:
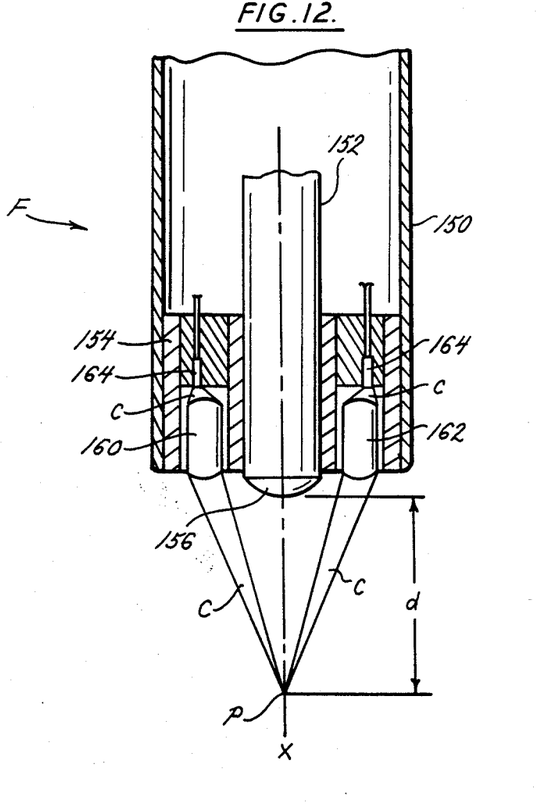
FIG. 12 is a sectional view of another modified measuring apparatus.

The bushing 154 contains two lenses 160 and 162 arranged on opposite sides of the optical axis x, that is at 180° intervals, and behind each lens 160 and 162 is a point source of light 164, which may be the end of an illuminated optical fiber. The two sources of light 164 are positioned with respect to their respective lenses 160 and 162 such that the light beams c emitted from each, after passing through the lenses 160 and 162, come into focus at a common point p along the optical axis x and that point p lies at a fixed distance d from the distal end of the scope 152.

The apparatus F is inserted into the cavity B and manipulated to bring the lesion D into the field of view f for the scope 152. Unless the distal end of the scope 152 is the distance d from the lesion D, the sources of light 164 will cast two somewhat out-of-focus spots of light on the lesion C or nearby tissue. Indeed, the apparatus 7 must be moved toward or away from the lesion C until the spots of light merge at a single focused spot along the optical axis x. When this occurs the distal end of the scope 152 is the known distance d from the lesion C. At this time, the width of the lesion C may be read from the graduated scale r in the eyepiece 154. The apparatus F is suitable for measuring only along surfaces that are oriented generally normal to the optical axis x, inasmuch as such surfaces will reflect light at the optical axis x, whereas a long narrow cavity will not.

The principles of the present invention may be utilized with scopes that have lateral or oblique fields of view or even with flexible scopes.

This invention is intended to cover all changes and modifications of the example of the invention herein chosen for purposes of the disclosure which do not constitute departures from the spirit and scope of the invention.

What is claimed is:

1. A measuring apparatus for measuring the distance between two locations on a surface without actually contracting the surface at those locations, said measuring apparatus comprising: a scope through which one may look to observe the surface, that scope having a distal end which is presented toward the surface to be observed and a proximal end that is located remote from the surface, the scope further having an optical axis and providing a field of view which lies beyond its distal end, the scope displaying reference marks within the field of view; a source of light; optical measuring means for projecting light derived from the source of light into the field of view to at least two regions spaced around the optical axis, for within each region presenting the light at localized areas spaced differently from the optical axis, for changing the localized areas at which the light is presented in each region, and for correlating the localized areas with units of linear measure, so that when the light at two localized areas is reflected from the surface within the field of view and the localized areas align with the reference marks, the distance between the two localized areas from which the light is reflected is known.

2. The apparatus according to claim 1 wherein the light source is located remotely from the distal end of the scope.

3. The apparatus according to claim 2 wherein the optical measuring means divides the light from the source into two beams and projects one beam into one region and the other into the other region.

4. The apparatus according to claim 3 wherein the optical measuring means includes a separate lens at each region where the two beams are projected into the field of view and a plurality of light emitting points behind each lens from which light from the source may appear, with the lens projecting light from each point to a different localized area beyond the lens and within the field of view.

5. The apparatus according to claim 4 wherein the optical measuring means includes a header presented opposite the light source such that the light from the source is cast upon a very small area of the header; wherein the header has a light receiving point located in it with each light receiving point corresponding to a light emitting point at a lens in the sense that when the light receiving point is illuminated, the corresponding light emitting point projects a beam into the lens; wherein the light source illuminates more than one, but substantially less than all, of light-receiving points at any time; and wherein the optical measuring means further includes means for connecting corresponding light receiving and light emitting points for transferring light from the former to the latter, and means for changing the light-receiving points illuminated by the light source, whereby the locations at which the light is presented within the field of view may be altered.

6. The apparatus according to claim 5 wherein the means for connecting corresponding light receiving and light emitting points comprises optical fibers, there being a different optical fiber between each light-receiving point and its corresponding light emitting point.

7. The apparatus according to claim 3 wherein the optical measuring means includes a separate lens at each region where the two beams are projected into the field of view, and means for moving the beams relative to the respective lenses toward and away from the optical axis.

8. The apparatus according to claim 7 wherein the optical measuring means includes optical fibers, one leading to each lens and each emitting one of the light beams from its end, and the means for moving the beams moves the ends of the fibers.

9. The apparatus according to claim 8 wherein the lenses are within a mounting element that lies on both sides of the optical axis and contains slots which are directed radially with respect to the optical axis, with the slots being located behind the lenses; and wherein the ends of the optical fibers are in the slots.

10. The apparatus according to claim 9 wherein the means for moving the beams includes a pair of concentric tubes connected together by threads so that rotation of one tube relative to the other effects an axial displacement of that tube relative to the other, one of the tubes having a shoulder; wherein the mounting element is attached to one of the tubes with its slots presented toward the shoulder; and wherein the optical fibers are mounted such that for the most part they cannot be displaced axially with respect to the other tube, but near their ends, where they project into the slots, they bear against the shoulder on the one tube, so that axial displacement of the shoulder relative to the optical fibers will cause the ends of the fibers to move radially within the radial slots.

11. The apparatus according to claim 1 wherein the scope includes means for illuminating the field of view, and wherein the light presented at the localized areas when reflected from a surface in the field of view is visible in the field of view.

12. The apparatus according to claim 1 and further comprising a hollow sheath through which the scope extends, with the scope being smaller than the interior of the sheath so that a space exists between the interior of the sheath and the scope, and means for locating the scope in a fixed position within the sheath without obstructing the passage of fluid through the sheath.

13. A measuring apparatus for measuring the distance between two locations on a surface without actually contacting the surface at those locations, said apparatus comprising: a scope having a distal end where the scope is provided with an objective lens and a proximal end where the scope is provided with an eyepiece which aligns with the objective lens along an optical axis, such that one can observe through the eyepiece that which lies within a field of view located beyond the objective lens, whereby one may observe the surface from a location remote from the surface when the objective lens is presented toward the surface, the scope further displaying spaced apart reference marks within the field of view, there being a reference mark on each side of the optical axis; a source of light located remote from the distal end of the scope; a header presented opposite the source of light such that the light is cast upon its, the header having light-receiving points arranged in two groups such that the light cast by the source of light simultaneously illuminates one point in each group; positioning means for changing the light-receiving points illuminated by light source; light-emitting points arranged in two groups with one group being on one side of the optical axis and the other group being on the other side of the optical axis, each light-emitting point being connected with a corresponding light-receiving point, such that, when the light-receiving point is illuminated, the corresponding light-emitting point will project light into the field of view, the light that is projected being capable of being observed through the scope as a localized area of light when reflected from a surface in the field of view, the light-emitting points of each group illuminating localized areas that are spaced differently from the optical axis, for each pair of light-receiving points illuminated simultaneously by the light source, one of the corresponding light-emitting points being in one group at the distal end of the scope and the other of the corresponding light-emitting points being in the other group at the distal end of the scope, so that when the positioning means changes the light-receiving points that are illuminated, different light-emitting points project light into the field of view and are capable of illuminating different localized areas in the field of view; and means for correlating the light-receiving points which are illuminated by the light source with the space between the localized areas that are illuminated in the field of view by the corresponding light-emitting points when such localized areas appear to align with the reference marks; whereby, the space between two locations on a surface within the field of view may be determined by bringing the reference marks into alignment with the two locations and adjusting the positioning means until it selects light-receiving points which correspond with light-emitting points that illuminate localized areas coinciding with the two locations.

14. The apparatus according to claim 13 wherein each light-receiving point and its corresponding light-emitting point are connected by an optical fiber.

15. The apparatus according to claim 13 and further comprising a terminal block on each side of the scope at its distal end, with each terminal block holding the light-emitting points of one of the groups, the light-emitting points in each terminal block being arranged in a line, one after the other, generally radially with respect to the optical axis.

16. The apparatus according to claim 15 and further comprising a lens in front of each terminal block, such that each light-emitting point, when illuminated projects light through the lens that is in front of its terminal block.

17. The apparatus according to claim 16 and further comprising a header which holds the light-receiving points, and the positioning means causes a displacement between the header block and the light source to enable the light source to illuminate different pairs of light-receiving points.

18. The apparatus according to claim 13 and further comprising a header which holds the light-receiving points and the positioning means causes a displacement between the header block and the light source to enable the light source to illuminate different pairs of light-receiving points.

19. The apparatus according to claim 13 and further comprising a hollow sheath located around the scope, the sheath having a passageway from one end to the other.

20. The apparatus according to claim 13 wherein the scope includes means for illuminating the field of view.

21. A process for measuring the distance between two locations on a surface that is within a cavity without contacting the surface at those locations, said process comprising: inserting a scope into the cavity, with the scope providing a field of view and displaying reference marks on which appear within the field of view on each side of its optical axis; on each side of the scope projecting light through a lens and into the field of view; bringing the light substantially into focus on a surface within the field of view and aligning the marks within the scope with the region of the surface that is to be measured.

22. A measuring apparatus for measuring the distance between two locations on a surface without actually contacting the surface at those locations, said measuring apparatus comprising: a scope through which one may look to observe the surface, that scope having a distal end which is presented toward the surface to be observed and a proximal end that is located remotely from the surface, the scope further having an optical axis and providing a field of view which lies beyond its distal end, the scope displaying reference marks within the field of view on each side of the optical axis; a source of light located along each side of the scope; a lens located in front of each source of light such that each lens projects its source of light into the field of view where the light from the two sources of light will come into focus at a single location on the surface to form a point of light, whereby by correlating the reference marks with the surface it is possible to make measurements generally perpendicular to the optical axis.

* * * * *

UNITED STATES PATENT AND TRADEMARK OFFICE
CERTIFICATE OF CORRECTION

PATENT NO. : 4,958,932

DATED : September 25, 1990

INVENTOR(S) : Jerry T. Kegelman; Joseph C. Kroutil; Rodney Lusk

It is certified that error appears in the above-identified patent and that said Letters Patent is hereby corrected as shown below:

Column 7, line 17, after "This" delete "is".

Column 9, line 20, after "ratus" delete "7" and insert
--- F ---.

Claim 13, Column 11, line 25, after "upon" delete "its" and insert --- it ---.

Claim 21 should be as follows:

21. A process for measuring the distance between two locations on a surface that is within a cavity without contacting the surface at those locations, said process comprising: inserting a scope into the cavity, with the scope providing a field of view in which the surface lies and displaying reference marks which appear within the field of view on each side of its optical axis; on each side of the optical axis projecting light through a lens and into the field of view, which light comes into focus as points of light, the distance between which points is known; bringing

UNITED STATES PATENT AND TRADEMARK OFFICE
CERTIFICATE OF CORRECTION

PATENT NO. : 4,958,932
DATED : September 25, 1990
INVENTOR(S) : Jerry T. Kegelman; Joseph C. Kroutil; Rodney Lusk It is certified that error appears in the above-identified patent and that said Letters Patent is hereby corrected as shown below:

the light substantially into focus on the surface within the field of view and aligning the reference marks that appear within the scope with the points of light and the region of the surface that is to be measured.

Signed and Sealed this

Tenth Day of December, 1991

Attest:

HARRY F. MANBECK, JR.

*Attesting Officer*     *Commissioner of Patents and Trademarks*